United States Patent
Turtzo (10) Patent No.: US 8,375,485 B2
(45) Date of Patent: Feb. 19, 2013

(54) SYSTEM, METHOD AND APPARATUS FOR TREATING BACK PAIN DURING REST

(75) Inventor: Craig Turtzo, Tarpon Springs, FL (US)

(73) Assignee: Anodyne Therapy, L.L.C., Tampa, FL (US)

( * ) Notice: Subject to any disclaimer, the term of this patent is extended or adjusted under 35 U.S.C. 154(b) by 304 days.

(21) Appl. No.: 12/849,831

(22) Filed: Aug. 4, 2010

(65) Prior Publication Data

US 2012/0030872 A1 Feb. 9, 2012

(51) Int. Cl.
A47C 21/04 (2006.01)

(52) U.S. Cl. .................................. 5/421; 5/690

(58) Field of Classification Search ........... 5/690, 600, 5/421; 607/100
See application file for complete search history.

(56) References Cited

U.S. PATENT DOCUMENTS

| | | | |
|---|---|---|---|
| 3,721,799 A * | 3/1973 | Carlstrom | 219/212 |
| 4,646,743 A | 3/1987 | Parris | |
| 4,930,504 A | 6/1990 | Diamantopoulos et al. | |
| 5,259,380 A | 11/1993 | Mendes | |
| 5,358,503 A | 10/1994 | Bertwell et al. | |
| 5,500,009 A | 3/1996 | Mendes | |
| 6,471,716 B1 | 10/2002 | Pecukonis | |
| 6,582,456 B1 * | 6/2003 | Hand et al. | 607/108 |
| 6,602,275 B1 | 8/2003 | Sullivan | |
| 6,607,550 B1 | 8/2003 | Bertwell | |
| 6,629,971 B2 | 10/2003 | McDaniel | |
| 6,663,659 B2 | 12/2003 | McDaniel | |
| 6,676,655 B2 | 1/2004 | McDaniel | |
| 6,881,983 B2 | 4/2005 | Narayan et al. | |
| 2004/0231056 A1 * | 11/2004 | Jansen | 5/600 |

* cited by examiner

Primary Examiner — Robert G Santos
Assistant Examiner — Brittany Wilson
(74) Attorney, Agent, or Firm — Larson & Larson, P.A.; Frank Liebenow (57) ABSTRACT

An application for a system, method and apparatus that directs light and heat towards an area of pain of a person while the person rests on a section of furniture (e.g., sleeps on a mattress). The light and heat are provided by an array of LEDS that are removably situated within a cavity that is, for example, formed or cut into the furniture/mattress.

16 Claims, 10 Drawing Sheets

SYSTEM, METHOD AND APPARATUS FOR TREATING BACK PAIN DURING REST

CROSS-REFERENCE TO RELATED APPLICATION

This application is related to U.S. patent application titled "HEAT AND LIGHT-EMITTING PAD," Ser. No. 12/849,833 filed even date here within. This application is also related to U.S. patent application titled "INTEGRATED SYSTEM, METHOD AND APPARATUS FOR TREATING BACK PAIN DURING REST," Ser. No. 12/849,835 filed even date here within. This application is also related to U.S. patent application titled "WORN HEAT AND LIGHT-EMITTING DEVICE," Ser. No. 12/849,836 filed even date here within.

FIELD

This invention relates to the field of pain relief and more particularly to a system for the deliver of heat and infrared light to a user for the relief of pain.

BACKGROUND

It is known that exposure to heat and certain wavelengths of light are useful to temporarily increase local circulation, reduce pain and to enhance healing as detailed in Michlovitz and Nolan, Modalities for Therapeutic Intervention (4th Ed.), F. A. Davis Company (2005). Recent inventions have used light and/or heat as a therapeutic device for the relief of pain. In particular, it has been shown that infra-red and near infrared light of certain wavelengths possess therapeutic qualities. Exposure to certain wavelengths of light is known to alleviate various effects that sun exposure, gravity, pollution and chemicals have on the skin.

LED Devices that emit infrared wavelengths of light are well known and are capable of providing sufficient light for therapeutic effects to persons exposed to the light under certain conditions. Additionally, such LED Devices also emit heat, which also provide therapeutic effects such as reducing pain in certain situations. Existing stand-alone LED devices do not provide for sufficiently convenient at-home applications of infrared light and heat. For example, cable-connected devices are available having multiple LED arrays for the irradiation of a user's leg or foot, but the cable causes problems as the user moves. Likewise, battery powered devices also having multiple LED arrays for the irradiation of a user's foot or leg improve upon this problem, but the batteries cause an issue by presenting hard bulges that exert pressure on the user when the user rests in certain positions.

What is needed is a system that will irradiate a locale of a user with heat and light while the user rests.

SUMMARY OF THE INVENTION

The present invention includes a system, method and apparatus for directing light and heat towards an area of pain of a person while the person rests on a section of furniture (e.g., sleeps on a mattress). The light and heat is provided by an array of LEDS that are removably situated within a cavity that is, for example, formed or cut into the section of furniture/mattress.

In one embodiment, a system for providing heat and light to a person for the purpose of treating pain is disclosed including a section of furniture for supporting the person. The section of furniture has a cavity located on a surface which contacts the person and an array of LEDS is fit snuggly within the cavity and is removable from the cavity. The LEDS are positioned within the cavity to direct light and heat towards an area of pain of the person.

In another embodiment, a method of reducing pain in a person is disclosed including providing a section of furniture for supporting the person. The section of furniture has a cavity located on a surface which contacts the person. An array of LEDS is snuggly fit within the cavity and are also removable from the cavity. The LEDS are positioned to direct light and heat towards an area of pain of the person. The person rests on the section of furniture for a period of time in which the array of LEDS emit light and heat for at least a portion of the period of time of rest.

In another embodiment, an apparatus for providing heat and light to a person for the purpose of treating pain is disclosed including a section of furniture. The section of furniture supports the person and has a cavity or other receptacle for removably containing an array of LEDS. The array of LEDS fit snuggly within the cavity or other receptacle and are removable. The LEDS within the array are positioned to direct light and heat towards an area of pain of the person. It is anticipated that the section of furniture is either a portion of the furniture such as a mattress, cushion, etc, or the section of furniture is the entire furniture such as a foam chair, etc.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments, examples of which are illustrated in the accompanying drawings. Throughout the following detailed description, the same reference numerals refer to the same elements in all figures.

Throughout this description, a mattress (bed) is used as an example of furniture. This is but an example and it is anticipated that the present method, apparatus and system be used in conjunction and/or integrated into any type of human-supporting or contact furniture such as pillows, chairs, recliners, couches, sofas, futons, car/vehicle seats etc. It is further anticipated that the present method, apparatus and system be applied to other devices/systems that normally contact the human body such as bicycle seats, motorcycle seats, arm rests, head rests, etc. When integrated into, for example, a pillow, the pillow is, for example, placed behind the back when the person is sitting in a chair for back pain or against the neck for neck pain.

Figure 1:
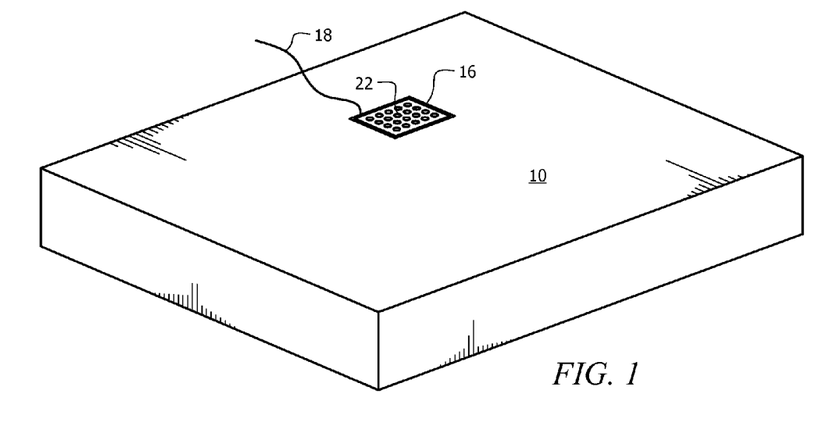
FIG. 1 illustrates a perspective view of a first embodiment.

Referring to FIG. 1, a perspective view of a first embodiment is shown. In this embodiment, an array of LEDS 22 is integrated into a treatment pad 16 that is positioned on, for example, a bed/mattress 10. The LEDS 22 are connected by a circuit board 84 and held in a soft, rubber/plastic holder 17 (see FIG. 16). In some embodiments, the thin pad 16, LEDS 22 and circuit board 84 are enclosed in a cloth cover for protection. The LEDS are powered through a cable 18 connected to a power supply/controller (see FIG. 13). The power supply/controller provides a controlled amount of electrical energy to the array of LEDS 22, causing the LEDS 22 to emit light at one or more wavelengths, preferably including infrared or near infrared. Additionally, the LEDS 22 produce heat. Both the light and heat provide therapeutic effect to a person in contact with the thin pad 16 of LEDS 22 when in contact with the person. It is anticipated that, for relief of back pain, the person positions themselves such that the person's back or lower back is located directly over the thin pad 16 of LEDS 22 (see FIGS. 9 and 10). The invention is anticipated to perform equally as well with other parts of the human body.

Figure 2:
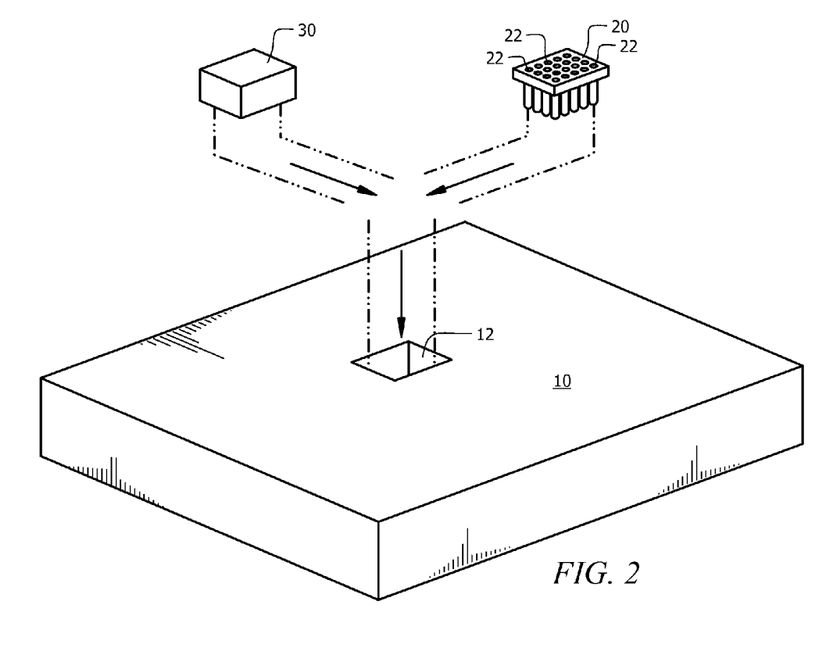
FIG. 2 illustrates a second perspective view of a second embodiment.

Referring to FIG. 2, a second perspective view of a second embodiment is shown. This embodiment includes a modular section within furniture such as a mattress 10. In such, a cavity 12 is made/formed/left in the furniture/mattress 10 into which an option module 30/20 is fit. In such, for deployment of the furniture/mattress 10 without the array 20 of LEDS 22, a blank insert 30 is placed in the cavity. Therefore, when the furniture/mattress 10 is covered (e.g., with a sheet 16—see FIG. 7) and the cavity 12 is filled with the blank insert, it is difficult to detect by a person using the furniture/mattress 10. Alternately, when the array 20 of LEDS 22 is to be used, the blank insert 30 is removed and the array 20 of LEDS 22 is inserted into the cavity 12 of the mattress/furniture 10. As shown in FIG. 2, the entire array 20 is populated with LEDS 22, preferably infrared or near-infrared LEDS 22 or a mixture of infrared or near-infrared LEDS 22 and/or visible light LEDS 22. Any wavelength of LEDS 22 is anticipated. In embodiments in which the furniture/mattress 10 is a mattress 10, it is anticipated that the mattress 10 comprise any known mattress material currently used in the industry, including foam rubber (e.g., latex foam), memory foam (visco-elastic memory foam material) and the like. Memory foam material is often made from synthetic polyurethane foam material with the addition of certain types of chemicals which increase the weight or density of the foam, as known in the industry. It is further anticipated that the mattress 10, in some embodiments, is an air mattress 10 and, therefore, the mattress 10 is completely sealed and air-tight around the cavity 12.

Figure 3:
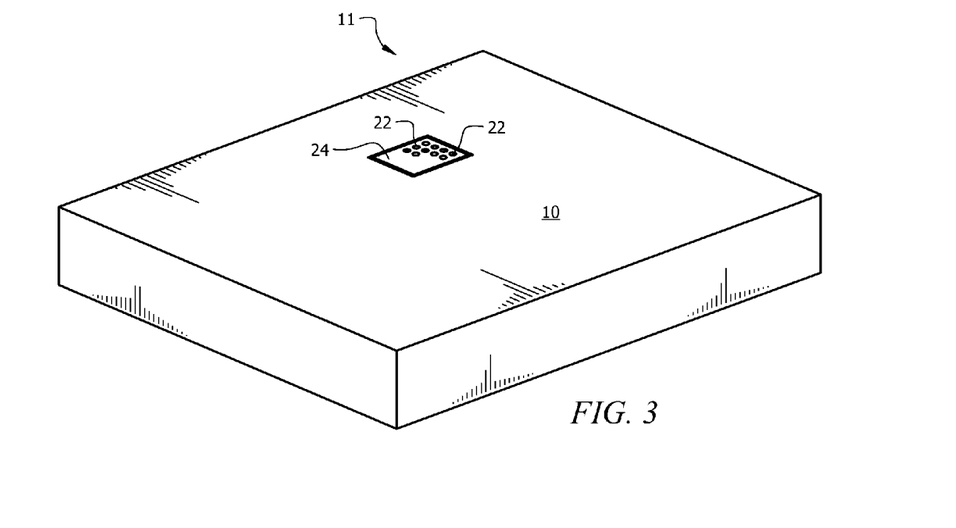
FIG. 3 illustrates a third perspective view of the second embodiment.
Figure 4:
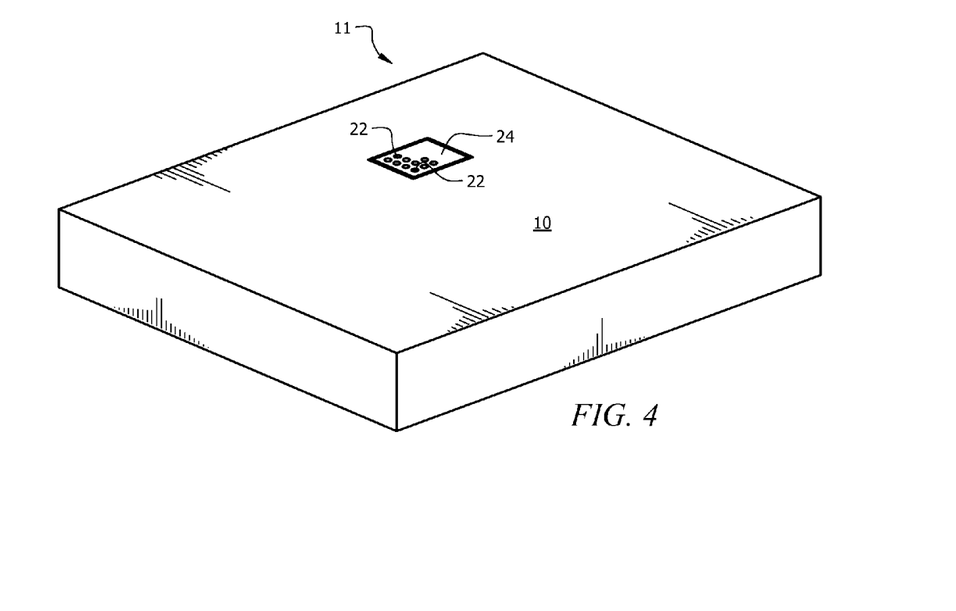
FIG. 4 illustrates a fourth perspective view of the second embodiment.

Referring to FIGS. 3 and 4, a third and fourth perspective view of the second embodiment is shown. In this the array 24 of LEDS 22 is populated with LEDS 22 towards one end of the array 24 and the array 24 is passive at the opposite end (absent of active LEDS). In such, when a shorter person uses the array 24, for example to relieve lower back pain, the array 24 is positioned in the mattress as shown in FIG. 3 and the active LEDS 22 are positioned toward the head of the bed 11, thereby aligning with the shorter person's lower back. Alternately, as shown in FIG. 4, when a taller person uses the array 24, for example to relieve lower back pain, the array 24 is turned 180 degrees within the mattress so that the active LEDS 22 are positioned away from the head of the bed 11, thereby aligning with the taller person's lower back.

Figure 5:
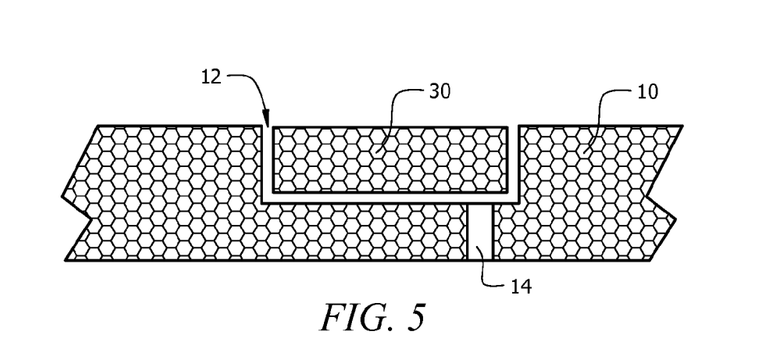
FIG. 5 illustrates a cross-sectional view of the second embodiment.

Referring to FIG. 5, a cross-sectional view of the second embodiment is shown. In this view, the blank insert 30 is snuggly fit within the cavity 12 (e.g. a tight fit limiting or reducing movement/sliding along any axis). In some embodiments, a hole or slot 14 connects the cavity with the bottom of the furniture/mattress 10 for running cables 26 (see FIG. 6).

Figure 6:
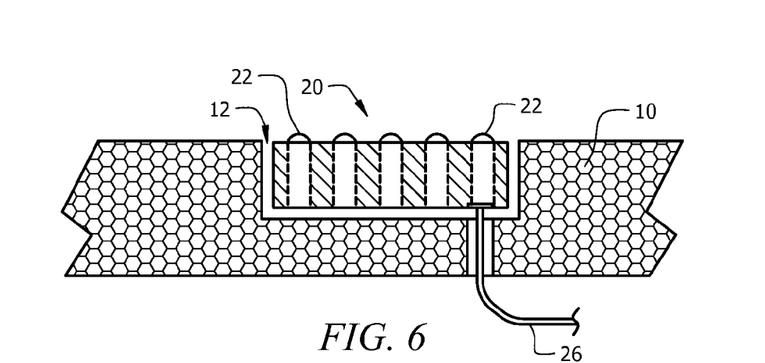
FIG. 6 illustrates a second cross-sectional view of the second embodiment.

Referring to FIG. 6, a second cross-sectional view of the second embodiment is shown. In this view, the array 20 of LEDS 22 is snuggly fit within the cavity 12 (e.g. a tight fit limiting or reducing movement/sliding along any axis). In some embodiments, an electrical cable 26 from the LEDS 22 to a controller 70 and/or power supply 74 (see FIGS. 12 and 13) exits through the hole or slot 14 connects the cavity with the bottom of the furniture/mattress 10 for running cables 26.

Figure 7:
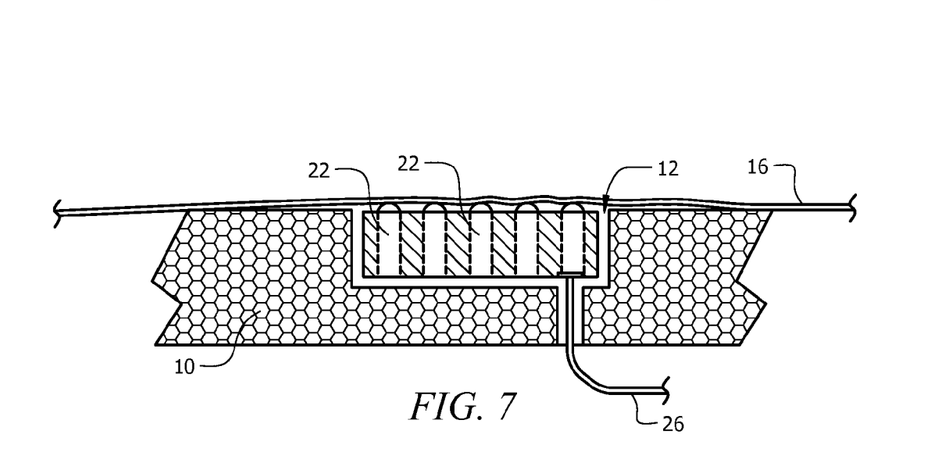
FIG. 7 illustrates a third cross-sectional view of the second embodiment.

Referring to FIG. 7, a third cross-sectional view of the second embodiment is shown. In this view, the array 20 of LEDS 22 is positioned within the cavity 12. In some embodiments, an electrical cable 26 from the LEDS 22 to a controller 72 and/or power supply 74 (see FIG. 13) exits through the hole or slot 14 that connects the cavity with the bottom of the furniture/mattress 10 for running cables 26. In this view, a cloth cover 16 is positioned over the array 20 of LEDS 22. Studies have shown that by increasing the power and/or duration of activity of the LEDS 22, sufficient heat and light penetrate layers of cloth 16 such as sheets, bedding, etc, and provide relief for pain such as lower back pain. Therefore, as shown in FIG. 7, the sheet 16 (for example) covers the LEDS 22 and the user positions their body such that the area in pain rests on top of the sheet 16 where the LEDS 22 lay beneath.

Figure 8:
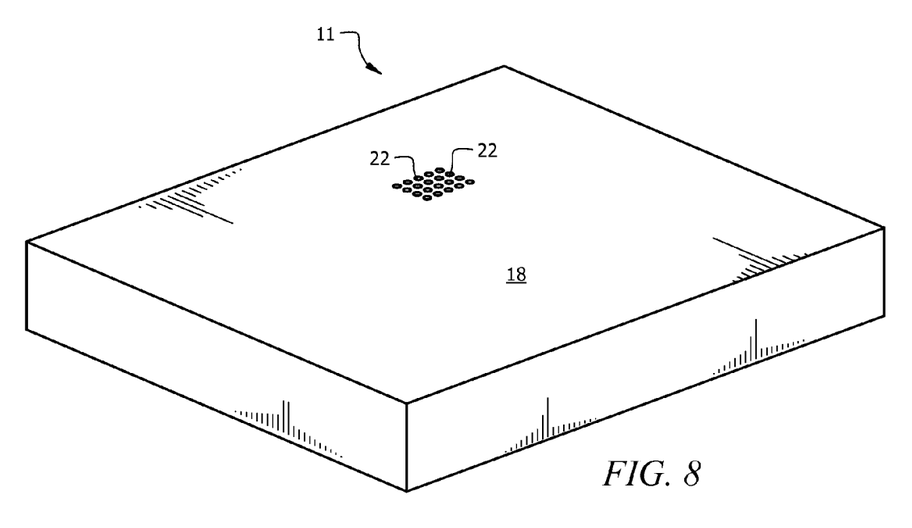
FIG. 8 illustrates a perspective view of a third embodiment.

Referring to FIG. 8, a perspective view of a third embodiment is shown. In this embodiment, a set of LEDS 22 are integrated directly into furniture/mattress 18. The LEDS 22 are fitted into holes or apertures of the mattress 18 and are in a fixed position relative to the head 11 of the mattress. Again, as in FIG. 7, it is anticipated that in some embodiments, a cloth cover 16 is positioned over the LEDS 22 and the power and/or duration of activity of the LEDS 22 is increased, providing sufficient heat and light to penetrate the layers of cloth 16 such as sheets, bedding, etc, and provide relief for pain such as lower back pain.

Figure 9:
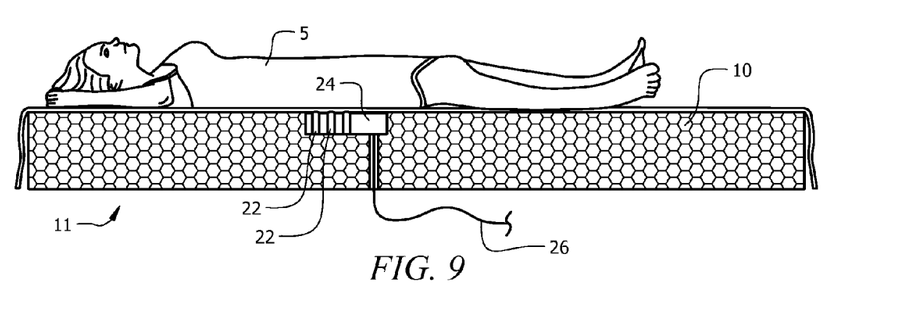
FIG. 9 illustrates a first cross-sectional view of the second embodiment in use.
Figure 10:
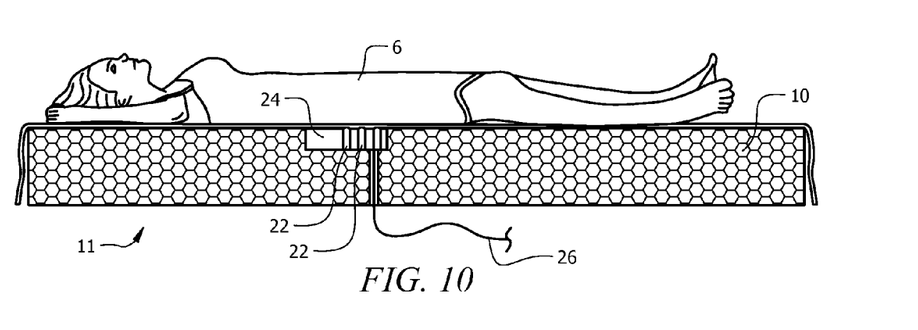
FIG. 10 illustrates a first cross-sectional view of the second embodiment in use.

Referring to FIGS. 9 and 10, a first and second cross-sectional view of the second embodiment in use is shown. In this the array 24 of LEDS 22 is populated with LEDS 22 towards one end of the array 24 and the array 24 is passive at the opposite end. In such, when a shorter person 5 uses the array 24, for example to relieve lower back pain, the array 24 is positioned in the mattress 10 as shown in FIG. 9 and the active LEDS 22 are positioned toward the head of the bed 11, thereby aligning with the shorter person's 5 lower back. Alternately, as shown in FIG. 10, when a taller person 6 uses the array 24, for example to relieve lower back pain, the array 24 is positioned in the mattress 10 so that the active LEDS 22 are positioned away from the head of the bed 11, thereby aligning with the taller person's 6 lower back.

Figure 11:
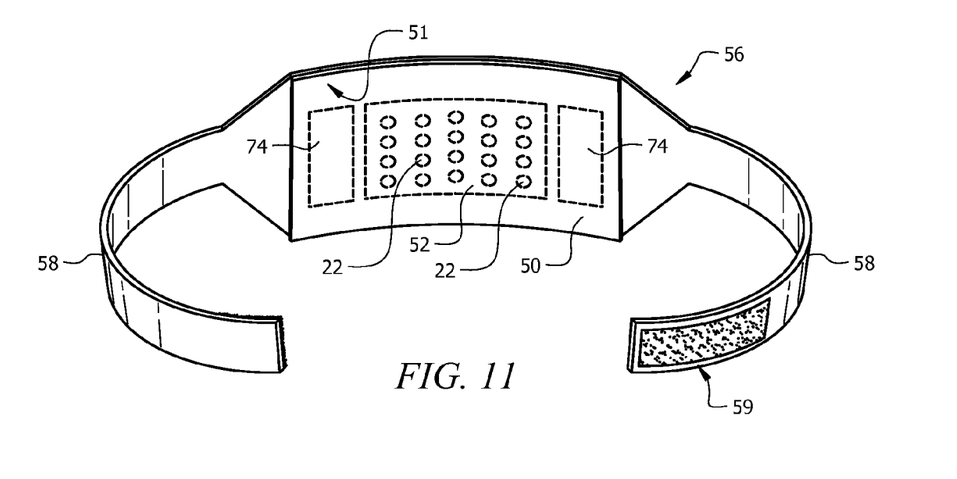
FIG. 11 illustrates a perspective view of a fourth embodiment.
Figure 12:
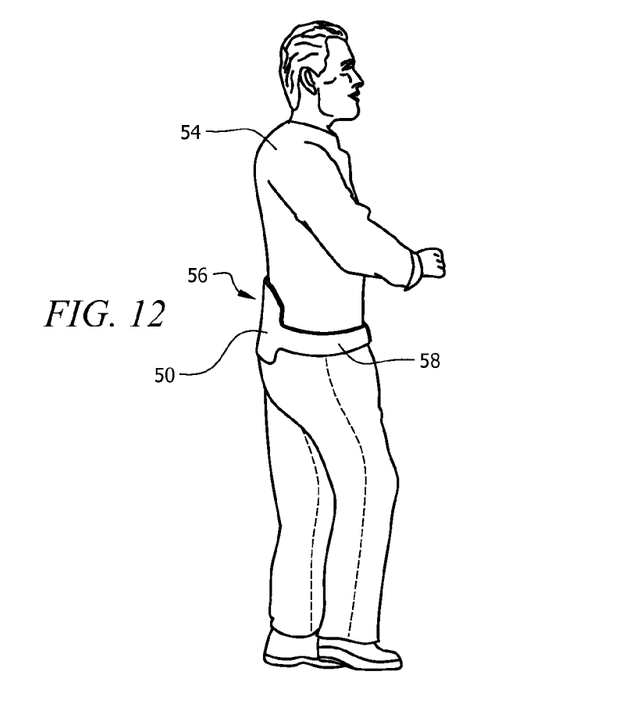
FIG. 12 illustrates a perspective view of a fourth embodiment in use.

Referring to FIGS. 11 and 12, perspective views of a fourth embodiment is shown. In this embodiment, an array 52 of LEDS 22 and power sources 74 are integrated into a wearable device 56 that attaches to a person's body 54 with a belt 58 and fastener 59. The belt 58 and fastener 59 are any such device as known in the industry and the exemplary hook and loop fastener 59 is one possible fastener. Other belt 58 lengths, widths and shapes are anticipated as well as other fasteners 59 such as buckles, buttons, snaps, etc.

In some embodiments, the array 52 of LEDS 22 and power sources 74 (e.g. batteries 74) are covered with a cloth material 51 such as nylon, silk, polyester, cotton, etc. As previously discussed, the power and/or duration of activity of the LEDS 22 is/are increased, providing sufficient heat and light to penetrate the layer of cloth 51 to provide relief for pain such as lower back pain as shown in FIG. 12. It is anticipated that the wearable device 56 of this embodiment is adaptable in size and shape to be worn on other parts of the body 54 such as feet, ankles, knees, legs, other areas of the back, neck, arms, hands and head. By situating the power source 74 (e.g. batteries 74) within the back area of the wearable device 56, heat emitted from the batteries as they discharge provides additional heat to, for example, the person's 54 back (see FIG. 12).

Figure 13:
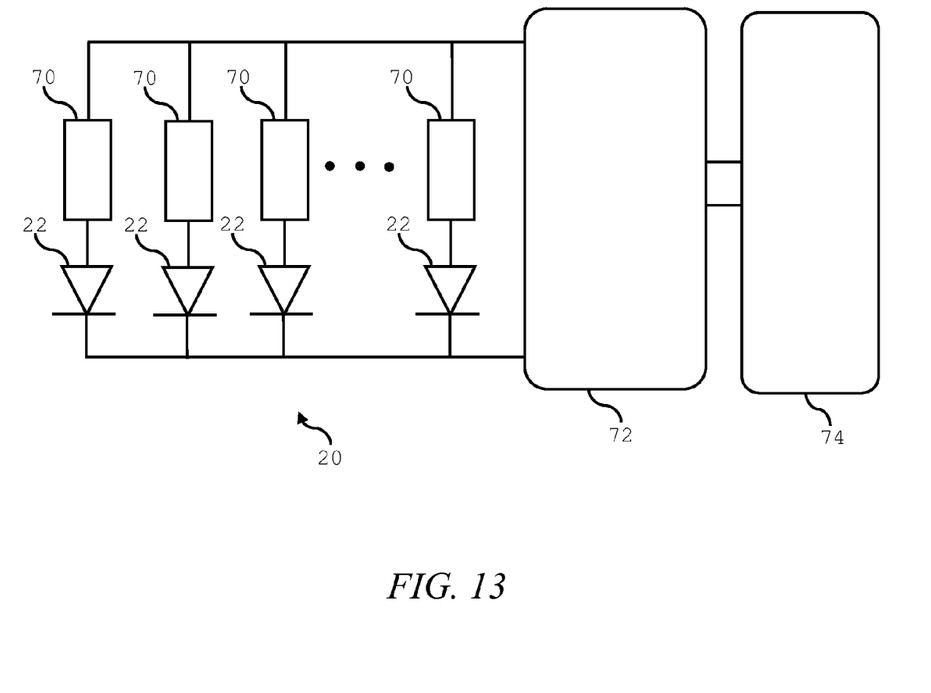
FIG. 13 illustrates a schematic view of an exemplary control system of all embodiments.

Referring to FIG. 13, a schematic view of an exemplary control system of all embodiments is shown. In this example, each LED 22 in the array 20 is current limited by an individual resistor 70. To illuminate the LEDS 22, a voltage is supplied by the controller 72 and the value of the resistors 70 determines the current flowing through each LED 22 and hence, the power output of each LED 22. The lower the resistance of each resistor 70, the higher the power output of its corresponding LED 22. This is an example of how such LEDS 22 are provided with a predetermined amount of power and other methods are well known using various combinations of LEDS 22 connected in series and/or parallel with various combinations of resistors 70 or other current controlling devices. In some embodiments, the current is directly controlled by the controller 72, eliminating the need for resistors 70. Any known system for providing a controlled amount of power to the LEDS 22 is anticipated here within.

As discussed previously, in applications in which a cloth 16/51 is situated between the user and the LEDS 22, the power to the LEDS 22 is increased to provide greater heat and light output to overcome the loss inserted by the cloth 16/51. This is accomplished in any way known in the industry including selecting lower resistance values of the resistors 70 or increasing the voltage output of the controller 72, etc.

The controller 72 provides power to the LEDS 22 during an active period. It is anticipated that the controller 72 provide power to the LEDS 22 for a pre-determined period of time from minutes up to continuously, as needed to address the user's specific pain. It is also anticipated that the controller 72 provide any known sequencing of power levels and timing as needed to address the specific pain. For example, for certain pain/healing operations, it is desired to alternate heat/cool and the controller 72 provides power for one period, thereby providing heat, and no or little power for another period, thereby removing the heat. Additionally, the controller 72, in some embodiments, provides pulse width modulation to control the power to the LEDS in which, the greater the pulse width, the greater the power supplied to the LEDS and the greater the light and heat intensity. In this embodiment, the pulse width and frequency is either fixed or variable.

For completeness, a power source 74 is shown, as known in the industry. Any known power source 74 is anticipated, including, but not limited to, a battery pack, a rechargeable battery pack and a power supply such as a power brick for converting household electric power into a DC voltage.

Figure 14:
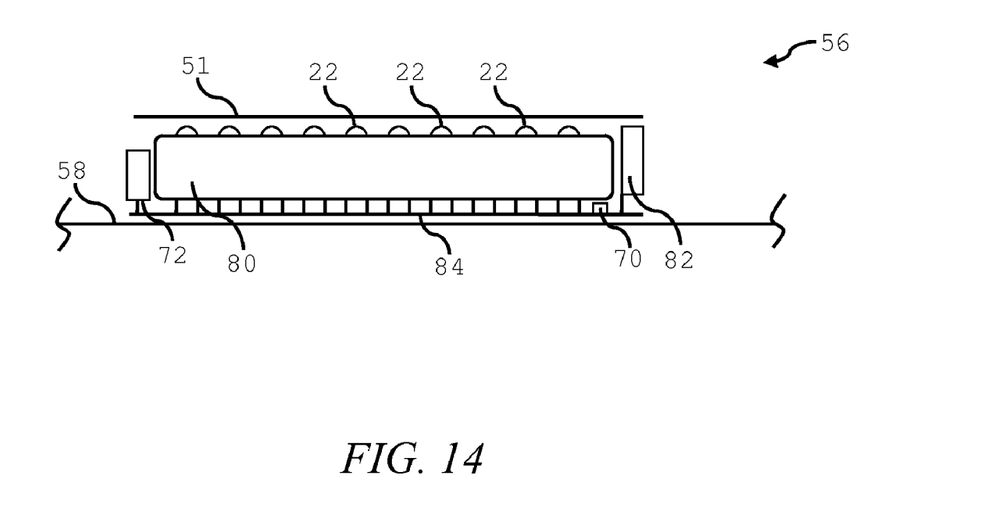
FIG. 14 illustrates a cutaway side plan view of an exemplary LED array and control system of all embodiments.

Referring to FIG. 14, a cutaway side plan view of an exemplary LED array control system of all embodiments is shown. In the preferred embodiment, the LEDS 22 are held in holes of a material 80, preferably a soft, sponge-like material that also conducts heat to provide a more even heat should one LED 22 heat more than another LED 22. The LEDs are physically and electrically interfaced to a circuit board 84 situated between the belt 58 and the LEDs 22/material 80. Other components such as the controller 72 and resistors 70 (if needed) are preferably mounted on the circuit board 84. Also connected to the circuit board 84 is a power switch 82 for signaling the controller 72 to enter an operating mode. Responsive to the user operating the power switch 82, the controller provides power to the LEDS 22. For example, after the user operates the power switch 82, the controller 72 provides power to the LEDS 22 for a fixed amount of time and then removes power to the LEDS 22 for another fixed amount of time, repeating this sequence for a pre-determined number of cycles. Although any switch 82 is anticipated, a proximity switch 82 is preferred to reduce the chance of the user inadvertently tripping the switch while wearing the belt 56. The proximity switch 82 preferably has hysteresis requiring the user to touch the proximity switch 82 for a time period before the operating mode is entered and requiring the user to again touch the proximity switch 82 for a time period before shutting off power. To inform the user that the operating mode has been entered or the system is shut off, a sounder 87 (see FIG. 15) is provided in some embodiments, preferably emitting one sound or sequence for entering the operating mode and another for power off.

In some embodiments, the LEDS 22 and power sources 74 (not visible in FIG. 14) are covered with a cloth material 51 such as nylon, silk, polyester, cotton, etc. As previously discussed, the power and/or duration of activity of the LEDS 22 is/are increased, providing sufficient heat and light to penetrate the layer of cloth 51 to provide relief for pain such as lower back pain. It is anticipated that the wearable device 56 of this embodiment is adaptable in size and shape to be worn on other parts of the body 54 such as feet, ankles, knees, legs, other areas of the back, neck, arms, hands and head. By situating the power source 74 (e.g. batteries 74) within the back area of the wearable device 56, heat emitted from the batteries as they discharge provides additional heat to, for example, the person's 54 back (see FIG. 12).

Figure 15:
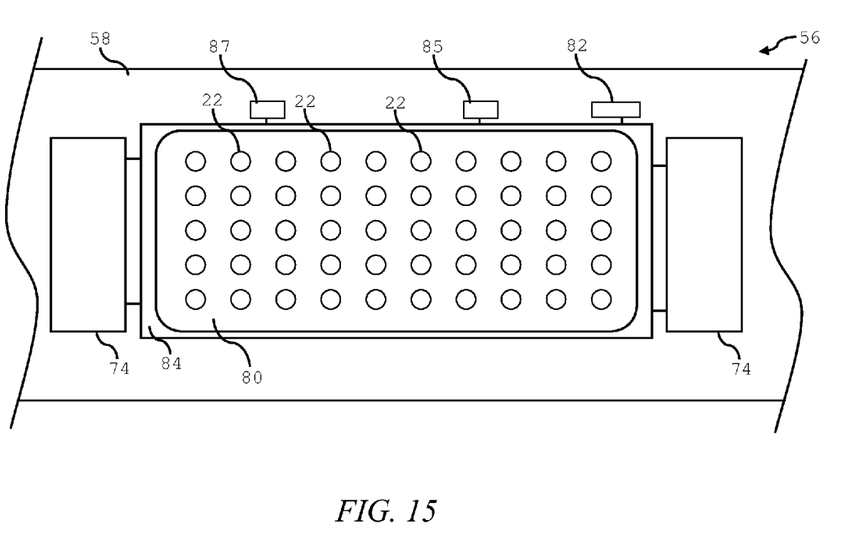
FIG. 15 illustrates a top plan view of an exemplary LED array and control system of all embodiments.

Referring to FIG. 15, a top plan view of an exemplary LED array control system of all embodiments is shown. In the preferred embodiment, the LEDS 22 are held in holes of a material 80, preferably a soft, sponge-like material that also conducts heat to provide a more even heat should one LED 22 heat more than another LED 22. The LEDs are physically and electrically interfaced to a circuit board 84 situated between the belt 58 and the LEDs 22/material 80. Other components such as the controller 72 and resistors 70 (if needed) are preferably mounted on the circuit board 84. The power source 74 (e.g. batteries 74) is electrically connected to the circuit board 84 the power source 74 (e.g. batteries 74) is situated within the back area of the wearable device 56. In some embodiments, the power source 74 is located near the circuit board 84 so that as the batteries 74 discharge, heat emitted provides additional heat to, for example, the person's 54 back (see FIG. 12).

Also connected to the circuit board 84 is a power switch 82 for signaling the controller 72 to enter an operating mode. Responsive to the user operating the power switch 82, the controller provides power to the LEDS 22. For example, after the user operates the power switch 82, the controller 72 provides power to the LEDS 22 for a fixed amount of time and then removes power to the LEDS 22 for another fixed amount of time, repeating this sequence for a pre-determined number of cycles. Although any switch 82 is anticipated, a proximity switch 82 is preferred to reduce the chance of the user inadvertently tripping the switch while wearing the belt 56. The proximity switch 82 preferably has hysteresis requiring the user to touch the proximity switch 82 for a time period before the operating mode is entered and requiring the user to again touch the proximity switch 82 for a time period before shutting off power. To inform the user that the operating mode has been entered or the system is shut off, a sounder 87 (see FIG. 15) is provided in some embodiments, preferably emitting one sound or sequence for entering the operating mode and another for power off.

The power source 74 is charged through a power connector 85 that is connected to an external power source (not shown) such as a wall-wart as known in the industry.

Figure 16:
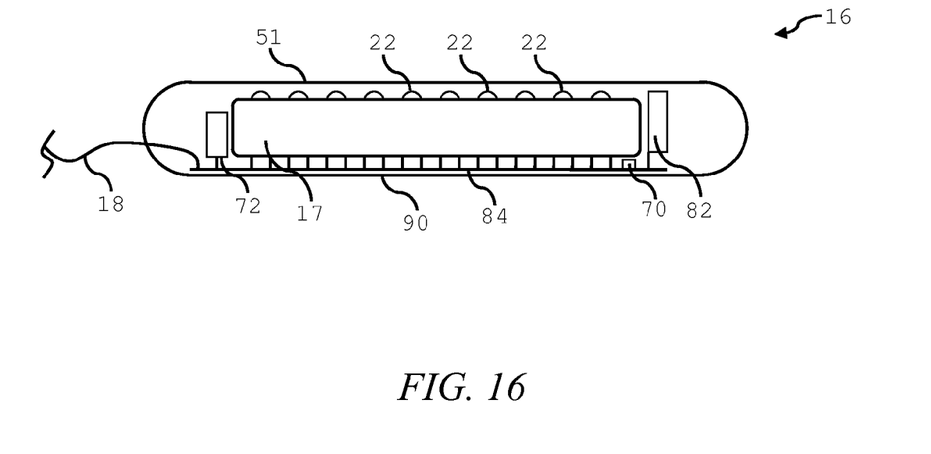
FIG. 16 illustrates a cutaway side plan view of an exemplary LED array and control system of the first embodiment.

Referring to FIG. 16, a cutaway side plan view of an exemplary LED array control system of the first embodiment is shown. In the preferred implementation, the LEDS 22 are held in holes of a material 17, preferably a soft, sponge-like material that also conducts heat to provide a more even heat should one LED 22 heat more than another LED 22. The LEDs are physically and electrically interfaced to a circuit board 84. Other components such as the controller 72 and resistors 70 (if needed) are preferably mounted on the circuit board 84. Also connected to the circuit board 84 is a power switch 82 for signaling the controller 72 to enter an operating mode. Responsive to the user operating the power switch 82, the controller provides power to the LEDS 22. For example, after the user operates the power switch 82, the controller 72 provides power to the LEDS 22 for a fixed amount of time and then removes power to the LEDS 22 for another fixed amount of time, repeating this sequence for a pre-determined number of cycles. Although any switch 82 is anticipated, a proximity switch 82 is preferred to reduce the chance of the user inadvertently tripping the switch while wearing the belt 56. The proximity switch 82 preferably has hysteresis requiring the user to touch the proximity switch 82 for a time period before the operating mode is entered and requiring the user to again touch the proximity switch 82 for a time period before shutting off power. To inform the user that the operating mode has been entered or the system is shut off, a sounder 87 (see FIG. 15) is provided in some embodiments, preferably emitting one sound or sequence for entering the operating mode and another for power off.

In some embodiments, the LEDS 22 and electronics 70/72/82/84 are enclosed within a cloth material 90 such as nylon, silk, polyester, cotton, etc. As previously discussed, the power and/or duration of activity of the LEDS 22 is/are increased, providing sufficient heat and light to penetrate the layer of cloth 90 to provide relief for pain such as lower back pain. It is anticipated that any number of LEDS 22 be present to cover a suitable area of the user's body. In some embodiments, power is provided by a power cable 18 connected to an external power source such as a power brick or wall-wart, as known in the industry.

Equivalent elements can be substituted for the ones set forth above such that they perform in substantially the same manner in substantially the same way for achieving substantially the same result.

It is believed that the system and method and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A system for providing heat and light to a person for the purpose of treating pain, the system comprising:
    a section of furniture, the section of furniture supporting the person;
    a cavity in the section of furniture, the cavity located on a surface of the section of furniture which contacts the person;
    an array of LEDS, the array of LEDS configured to fit within the cavity, the array of LEDS removable from the cavity, the LEDS within the array of LEDS positioned within the cavity to direct light and heat towards an area of pain of the person; and
    a blank insert, the blank insert sized to fit within the cavity, the blank insert placed in the cavity when the array of LEDS in not within the cavity.

2. The system of claim 1, wherein the furniture is a mattress.

3. The system of claim 1, wherein the LEDS emit heat and infrared light.

4. The system of claim 2, wherein the mattress has a head end and the LEDS are arranged on an outward surface of the array of LEDS and the LEDS are located near a first end of the array of LEDS leaving a blank end towards a distal second end of the array of LEDS such that, by rotating the array of LEDS 180 degrees within the cavity, the position of the LEDS with respect to the head end of the mattress is adjusted to account for a height of the person.

5. The system of claim 2, further comprising a sheet situated between the LEDS and the person, a power applied to the LEDS increased to compensate for heat and light loss caused by the sheet.

6. The system of claim 2, wherein the mattress is made of memory foam.

7. A method of reducing pain in a person, the method comprising:
    providing a section of furniture, the section of furniture supporting the person, the section of furniture having a cavity located on a surface of the section of furniture which contacts the person;
    providing an array of LEDS, the array of LEDS fitting within the cavity, the array of LEDS removable from the cavity, the LEDS within the array of LEDS positioned within the cavity to direct light and heat towards an area of pain of the person;
    providing a power to the LEDS, causing the LEDS to emit the light and the heat; and
    resting on the section of furniture by the person for a period of time, the array of LEDS emitting the light and the heat during a portion of the period of time;
    wherein the mattress has a head end and the LEDS are arranged on an outward surface of the array of LEDS and the LEDS are located near a first end of the array of LEDS leaving a blank end towards a distal second end of the array of LEDS such that, by rotating the array of LEDS 180 degrees within the cavity, the position of the LEDS with respect to the head end of the mattress is adjusted to account for a height of the person.

8. The method of claim 7, wherein the furniture is a mattress of a bed.

9. The method of claim 7, wherein the LEDS emit heat and infrared light.

10. The method of claim 7, further comprising a blank insert, the blank insert sized to fit within the cavity, the method further comprising the steps of removing the array of LEDS from the cavity and inserting the blank insert into the cavity.

11. The method of claim 8, further comprising a sheet situated between the LEDS and the person and the method further comprising the step of increasing the power applied to the LEDS to compensate for reductions of the heat and the light introduced by the sheet.

12. The method of claim 8, wherein the period of time is when the person is sleeping and the portion of the period of time is less than or equal to the period of time when the person is sleeping.

13. An apparatus for providing heat and light to a person for the purpose of treating pain, the apparatus comprising:
   a section of furniture, the section of furniture supporting the person, the section of furniture having a means for removably containing an array of LEDS, the array of LEDS configured to fit within the means for removably containing, the array of LEDS removable from the means for removably containing, the LEDS within the array of LEDS positioned within the means for removably containing to direct light and heat towards an area of pain of the person;
   a controller operably connected to the LEDS, providing power to the LEDS, responsive to the power, the LEDS emit the light and the heat; and
   wherein the furniture is a mattress and a sheet situated between the array of LEDS and the person, whereas the power applied to the LEDS is increased to compensate for reductions in the heat and the light caused by the sheet.

14. The apparatus of claim 13, wherein the LEDS are infrared LEDS and the light is infrared light.

15. The apparatus of claim 13, further comprising a blank insert, the blank insert sized to fit snuggly within the means for removably containing, the blank insert placed in the means for removably containing when the array of LEDS in not within the means for removably containing.

16. The apparatus of claim 13, wherein the mattress has a head end and the LEDS are arranged on an outward surface of the array of LEDS and the LEDS are located near a first end of the array of LEDS leaving a blank end towards a distal second end of the array of LEDS such that, by rotating the array of LEDS 180 degrees within the means for removably containing, the position of the LEDS with respect to the head end of the mattress is adjusted to account for a height of the person.

* * * * *